United States Patent [19]

Taylor

[11] 4,413,996
[45] Nov. 8, 1983

[54] DIAPER WITH LIQUID RETAINING CHAMBER

[76] Inventor: Kevin D. Taylor, 1716 N. 1900 West, Ogden, Utah 84404

[21] Appl. No.: 283,291

[22] Filed: Jul. 14, 1981

[51] Int. Cl.³ ............................................. A41B 13/02
[52] U.S. Cl. .................................................... 604/382
[58] Field of Search ............... 128/284, 286, 287, 288, 128/290 R, 290 H, 291, 289; 604/358, 378, 379, 382

[56] References Cited

U.S. PATENT DOCUMENTS

| | | | |
|---|---|---|---|
| 2,683,457 | 7/1954 | Cunningham | 128/290 R |
| 2,690,749 | 10/1954 | Nelson | 128/287 |
| 3,344,789 | 10/1967 | Arnold et al. | 128/287 |
| 3,441,024 | 4/1969 | Ralph | 128/287 |
| 4,019,517 | 4/1977 | Glassman | 128/290 R |
| 4,285,342 | 8/1981 | Mejek | 128/287 |

*Primary Examiner*—C. Fred Rosenbaum
*Attorney, Agent, or Firm*—Mallinckrodt, Mallinckrodt, Russell & Osburn

[57] ABSTRACT

A diaper for use upon an infant, comprising a sealed chamber for retaining excess liquids, formed between two moisture impervious sheets spaced apart by absorbent wadding, the innermost sheet having an opening therethrough for entry of the liquids into the reservoir. The diaper may further comprise a layer of conventional diaper wadding on the inside face of the innermost impervious sheet. The liquid capacity of the chamber is substantially greater than that of conventional wadding alone, so that diaper changes are needed less frequently. The infant is substantially protected from wetness by the barrier sheet.

4 Claims, 10 Drawing Figures

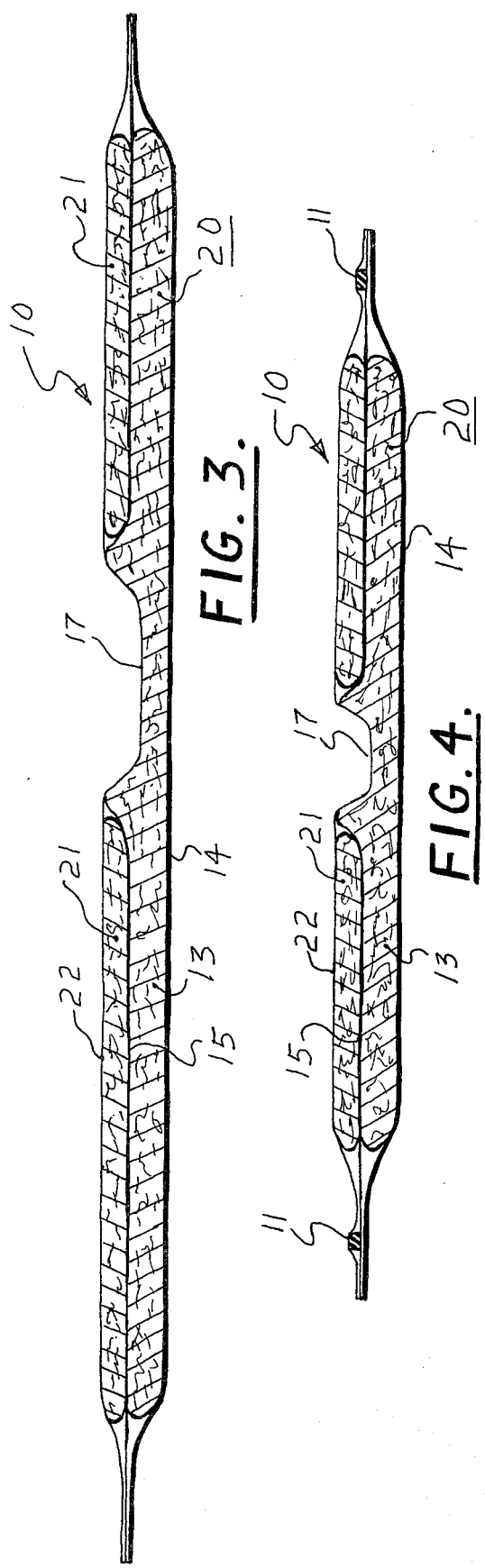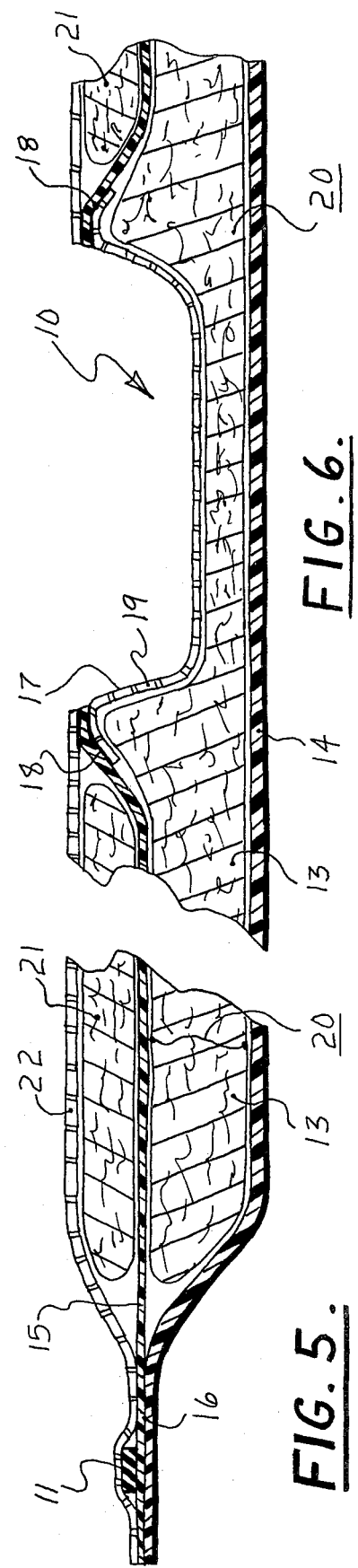

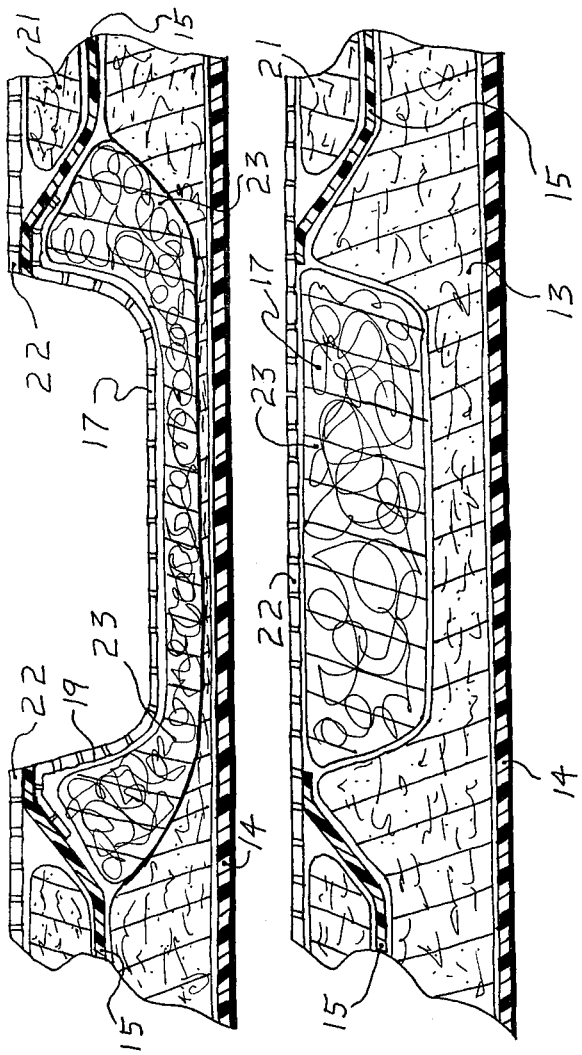
FIG. 7.
FIG. 8.
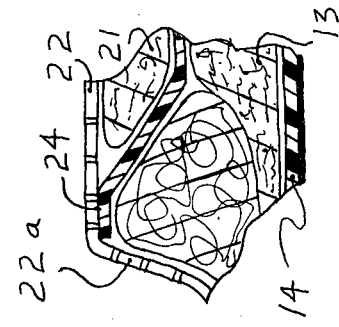
FIG. 10.
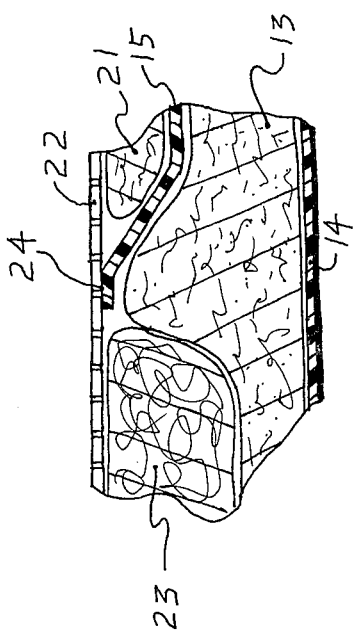
FIG. 9.

DIAPER WITH LIQUID RETAINING CHAMBER

BACKGROUND OF THE INVENTION

1. Field

The field of the invention is diapers for infants.

2. State of the Art

The original reuseable diaper was of washable cotton cloth in a simple rectangular shape, and has been almost entirely replaced by disposable diapers providing a layer of absorbent matting or wadding, covered by a relatively non-absorbent porous skin-side lining of non-abrasive material, sometimes quilted or dimpled, to reduce the contact of the infant's skin with the wet underlying matting. The shape has been adapted to be more comfortably form fitting, and adhesive strips have largely replaced pins as fasteners. A moisture impervious outside liner sheet is generally provided, and gentle elastic leg bands are often utilized to help to prevent leaking. U.S. Pat. Nos. Re. 26,151, 4,041,951 and 3,464,937 disclose representative prior art diaper constructions. These diapers depend upon the absorption capacity of the matting to retain the large amounts of moisture. Since the matting is quickly soaked beyond its capacity, the diaper must be changed frequently. The infant does not long remain dry, since the inside lining must be pervious to moisture, which can therefore flow from the wadding to the skin. The prior art diapers therefore provide no effective means for retaining excess moisture, nor for protecting the skin of the infant from wetness. Further, they inevitably leak after a period of use, even if leg bands are employed. To avoid bulkiness, and to provide economy, the matting is limited in thickness, with attendant limited moisture retention.

BRIEF SUMMARY OF THE INVENTION

With the foregoing in mind, the disadvantages in the prior art are eliminated or substantially alleviated by providing a diaper adapted to substantially prevent contact between the skin of the infant and is excreted liquids, and to provide a generally sealed retaining chamber therefor. Thus, the diaper retains increased quantities of such liquids, so that required diaper changes are less frequent than with prior art diapers. A flexible waterproof outside backing sheet and a waterproof inside barrier sheet are secured sealably together generally at their edges to provide the liquid retaining chamber. The waterproof sheets are spaced apart by a layer of absorbent matting loosely interposed therebetween, and the barrier sheet carries an opening positioned to allow entry of the liquids into the space between the waterproof sheets. Preferably, an inside layer of matting, covered by a non-abrasive skin contacting liner sheet, is provided between the barrier liner and the infant, to retain any spillage in the conventional manner. Preferably, a depression is formed in the outer layer at the liquid entrance, to provide a liquid receiving well to substantially prevent overflow into the inside layer. A portion of the outside layer around the well may advantageously be of substantially greater porosity than the bulk of the outer matting, to provide accelerated liquid flow into the chamber, or the well may be substantially filled with such material. In accordance with one aspect of the invention, the entire outer matting may be of material of substantially greater than conventional porosity.

BRIEF DESCRIPTION OF THE DRAWINGS

In the drawings, which represent the best mode presently contemplated for carrying out the invention.

DETAILED DESCRIPTION OF ILLUSTRATED EMBODIMENTS

Figure 1:
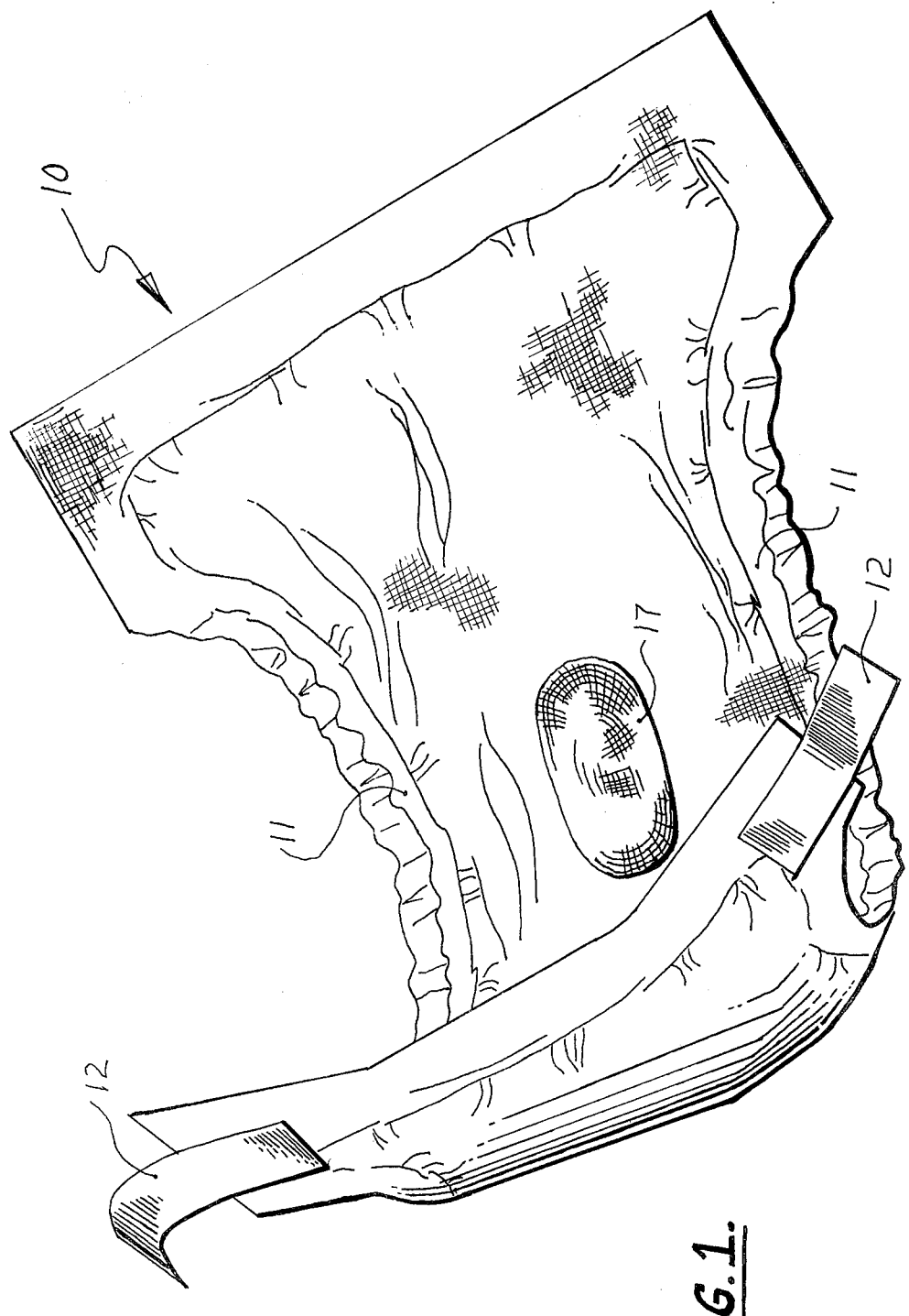
FIG. 1 is a perspective view of a diaper in accordance with the invention, curled as if being placed upon the body of an infant, drawn to a somewhat reduced scale, FIG. 2 a plan view of the diaper of FIG. 1 as seen from the inside thereof, generally flattened, a corner portion however represented upwardly curled and exploded, drawn to the same scale, FIG. 3 a cross sectional view of the diaper of FIG. 2 taken along line 3—3 thereof and drawn to the same scale, FIG. 4 a cross sectional view of the diaper of FIG. 3 taken along line 4—4 thereof, drawn to the same scale, FIG. 5 a cross sectional view of a fragment of the diaper of FIG. 4, drawn to an enlarged scale, FIG. 6 a cross sectional view of a fragment of the diaper of FIG. 3, drawn to the same scale as FIG. 5, FIG. 7 a cross sectional view of a fragment of a diaper of FIG. 1 illustrating another embodiment thereof, drawn to the scale of FIG. 5, FIG. 8 a cross sectional view of a fragment of the diaper of FIG. 1 illustrating still another embodiment in accordance with the invention, drawn to the scale of FIG. 5, FIG. 9 a cross sectional view of a fragment of the diaper of FIG. 8, drawn to the same scale and showing further structural details thereof, and FIG. 10 a cross sectional view of a fragment of the diaper of FIG. 1 constructed with the well lining sheet and the inside sheet integral, drawn to the scale of FIG. 5.
Figure 2:
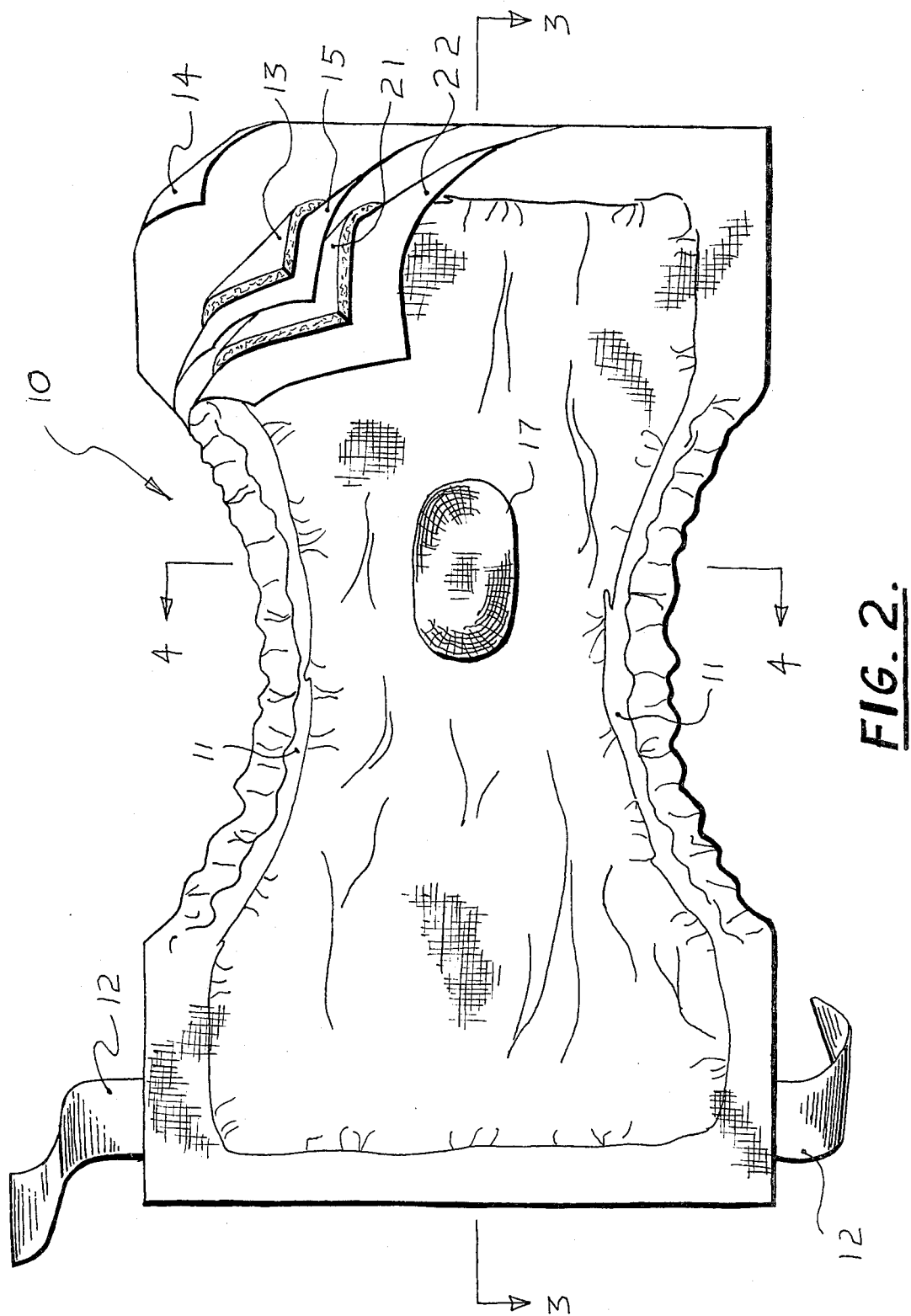

A diaper 10 with a liquid retaining chamber is shown in the figures, being, for illustrative purposes, of the form-fitting type and having elastic leg bands 11 and adhesive fasteners 12, (FIGS. 1 and 2) Diaper 10 comprises a layer 13 of moisture absorbent matting or wadding disposed unconnectedly between an outer, moisture impervious, thin flexible backing sheet 14 and a thin flexible, water impervious barrier sheet 15. Sheets 14 and 15 are sealably secured together around their peripheries, as by bonding 16. A liquid-receiving well 17 is formed within layer 13, positioned to directly receive a flow of liquid from the infant. (FIGS. 3–6) Barrier sheet 15 is discontinuous at well 17 and may be joined as by bonding 18 to a porous, liquid pervious well liner sheet 19. (FIG. 6)

When diaper 10 is in use, the flow of liquid into well 17 is quickly passed through well liner 19 into a chamber 20 formed between spaced sheets 14 and 15, held apart by wadding layer 13. Barrier 15 thereafter prevents contact between the liquid and the infant. To absorb small amounts of liquid which may splash or overflow from well 17, an inside matting layer 21 is provided upon barrier 15, preferably carrying a skin contacting porous sheet 22. Sheet 22 may be of the non-abrasive type used in prior art diapers to avoid irritation of the skin. Well covering sheet 19 may, if desired, be initially fabricated, such as by stretch forming, as an integral portion 22a of sheet 22. Barrier sheet 15 may be secured as by bonding 24 to inside sheet 21. (FIG. 10)

Sheets 14, 15, 19, and 22, although illustrated as having substantial thickness in certain figures, are preferably only a few thousandths of an inch thick, as with conventional diaper sheeting. Backing sheet 14 and barrier sheet 15 are preferably of flexible plastic. However, treated or coated waterproof cloth or the like may also be used.

The liquid holding capacity of chamber 20 is substantially greater than that of wadding 13 alone, since the space between sheets 14 and 15 adjusts as necessary to accommodate additional liquid. Also, the wadding 13 of the chamber 20 may be less dense, and its intersticial pores larger, than the prior art diapers, since capillary action is not essential for moisture retention within diaper 10. Therefore, coarser, lighter wadding 13 may be employed if desired and such wadding also facilitates rapid flow from well 17 into chamber 20. However, it is desirable that wadding 13 be dense enough to prevent excessive sloshing in chamber 20, and to inhibit any tendency for the liquid to flow back through well 17, when the infant assumes various positions or changes from one to another. As shown in FIG. 7, wadding 13 of conventional density and porosity may be employed along with a coarse wadding layer 23 surrounding well 17, the coarse wadding then facilitating flow into chamber 20, and layer 13 effectively inhibiting the aforesaid sloshing and flowback. Another embodiment (FIG. 8) employs very coarse wadding 23 with relatively large intersticial pores substantially filling well 17, layer 13 then preferably being of more clearly conventional density and porosity. With this illustrated embodiment of FIG. 8, sheet 22 may, as shown, extend uninterrupted across well 17, neither separate well lining sheet 19 nor pre-formed portion 22a of sheet 22 being required. The design and fabrication details of diaper 10 may be selected without departing from the essential spirit of the invention. FIG. 9 shows barrier 15 secured to a planar inside sheet 22 as by bonding 24, consistent with the embodiment illustrated in FIG. 7. FIG. 10 illustrates inside sheet 22 pre-formed to incorporate an integral liner for well 17.

It is evident that wadding of layer 13 may be selected from a wide range of materials, and from designs exhibiting a broad range of porosity and density. Conventional cellulose diaper wadding, perhaps selected for the desired porosity and moisture retention, is the more likely choice. The traditional cotton cloth diaper material would also function well. Natural or porous plastic sponge material could be used. Since this wadding 13 does not contact the skin, matting 13 of plastic, wood, and even metal strands could be used. Inside layer 21, however, is preferably of the conventional cellulose matting material.

The illustrated elastic leg bands 11, provided in prior art diapers to seal against leakage from oversaturated wadding, are not essential to the present invention. They may however be provided, to aid in retention of solids, and if desired, for neatness of fit and appearance. Diaper 10 may of course be adapted to pleated form fitting constructions, and even to the traditional simple rectangular shape, although form fitting features help to assure the proper location of well 17 upon the infant.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A diaper comprising:
    a thin flexible, moisture impervious backing sheet;
    a layer of porous fibrous material superimposed upon the backing sheet;
    a thin flexible moisture impervious barrier sheet generally covering the fibrous layer and sealably secured around its periphery to the backing sheet, said barrier sheet having a port therethrough positioned to allow entry of liquid from the body of the infant into the fibrous layer, the layer of fibrous material being dished toward the backing sheet at the port through the barrier sheet, so as to form a well for receiving the liquid;
    a thin flexible, water pervious well lining sheet covering the side and bottom portions of the well; and
    a well surrounding layer of porous fibrous material interposed between the well lining sheet and the adjacent porous fibrous material of the layer, said well surrounding layer being substantially more porous than the material upon the backing sheet, so that the liquid entering the well is immediately collected thereby.

2. A diaper comprising:
    a thin flexible, moisture impervious backing sheet;
    a layer of porous fibrous material superimposed upon the backing sheet;
    a thin flexible moisture impervious barrier sheet generally covering the fibrous layer and sealably secured around its periphery to the backing sheet, said barrier sheet having a port therethrough positioned to allow entry of liquid from the body of the infant into the fibrous layer, the layer of fibrous material being dished toward the backing sheet at the port through the barrier sheet, so as to form a well for receiving the liquid;
    a thin flexible, water pervious well lining sheet covering the side and bottom portions of the well;
    an inside layer of moisture absorbent material superimposed upon the barrier sheet, having an opening therethrough in general matching relationship to the port through the barrier sheet;
    a thin flexible, water pervious inside lining sheet superimposed upon the inside absorbent layer, having an opening therethrough in general matching relationship to the opening of the inside absorbent layer; and
    a well surrounding layer of porous fibrous material interposed between the well lining sheet and the adjacent porous fibrous material of the layer, said well surrounding layer being substantially more porous than the material upon the backing sheet, so that the liquid entering the well is immediately collected thereby.

3. A diaper comprising:
    a thin flexible, moisture impervious backing sheet;
    a layer of porous fibrous material superimposed upon the backing sheet;
    a thin flexible moisture impervious barrier sheet generally covering the fibrous layer and sealably secured around its periphery to the backing sheet, said barrier sheet having a port therethrough positioned to allow entry of liquid from the body of the infant into the fibrous layer, the layer of fibrous material being dished toward the backing sheet at the port through the barrier sheet, so as to form a well for receiving the liquid;

an inside layer of moisture absorbent material superimposed upon the barrier sheet, having an opening therethrough in general matching relationship to the part through the barrier sheet;

a pad of fibrous material substantially filling the liquid receiving well, being substantially more porous than the material upon the backing sheet; and a thin flexible, water pervious inside lining sheet superimposed upon the inside absorbent layer and the pad.

4. A diaper comprising:

a thin flexible, moisture impervious backing sheet;

a layer of porous fibrous material superimposed upon the backing sheet;

a thin flexible moisture impervious barrier sheet generally covering the fibrous layer and sealably secured around its periphery to the backing sheet, said barrier sheet having a port therethrough positioned to allow entry of liquid from the body of the infant into the fibrous layer, the layer of fibrous material being dished toward the backing sheet at the port through the barrier sheet, so as to form a well for receiving the liquid;

a thin flexible, water pervious well lining sheet covering the side and bottom portions of the well;

an inside layer of moisture absorbent material superimposed upon the barrier sheet, having an opening therethrough in general matching relationship to the port through the barrier sheet;

a thin flexible, water pervious inside lining sheet superimposed upon the inside absorbent layer, having an opening therethrough in general matching relationship to the opening of the inside absorbent layer; and a well surrounding layer of porous fibrous material interposed between the well lining sheet and the adjacent porous fibrous material of the layer, said well surrounding layer being substantially more porous than the material upon the backing sheet, so that the liquid entering the well is immediately collected thereby.

* * * * *